United States Patent [19]

Barber et al.

[11] 4,456,002

[45] Jun. 26, 1984

[54] SPRING METACARPOPHALANGEAL FLEXION SPLINT (KNUCKLE SPLINT)

[75] Inventors: Lois M. Barber, Pismo Beach; William H. Jackson, Atascadero, both of Calif.

[73] Assignee: L M B Hand Rehab Products, San Luis Obispo, Calif.

[21] Appl. No.: 424,202

[22] Filed: Sep. 27, 1982

[51] Int. Cl.³ .............................................. A61F 5/10
[52] U.S. Cl. .................................... 128/77; 128/87 A
[58] Field of Search ..................... 128/77, 87 R, 87 A; 272/67, 68, 140

[56] References Cited

U.S. PATENT DOCUMENTS

| | | | |
|---|---|---|---|
| 2,767,708 | 10/1956 | Keropian | 128/77 |
| 4,220,334 | 9/1980 | Kanamoto et al. | 128/77 X |
| 4,243,026 | 1/1981 | Barber | 128/87 A |

OTHER PUBLICATIONS

Glanville, H. J., "New Inventions", pp. 252, 253, The Lancet, Feb. 3, 1962.

Primary Examiner—John D. Yasko
Attorney, Agent, or Firm—George F. Bethel; Patience K. Bethel

[57] ABSTRACT

A spring metacarpophalangeal flexion splint designed for dynamically flexing the metacarpophalangeal joints without restricting normal hand use includes: a proximal phalangeal piece which is adapted to contact and cover the proximal phalanges of the hand and is formed of a resilient metal strip which is substantially covered with a pliant cushioning material; a palm piece adapted to fit into the palmar arch and crease of the hand and is made up of a rigid tube covered with a pliant cushioning material; and a pair of spaced apart generally parallel spring wires. The spring wires are disposed laterally with respect to the hand and connect the proximal phalangeal piece with the palm piece. A loop extension of the spring wires from the palm piece provides a means of attachment for a dorsal strap which is extended between the wires to permit the increase and decrease of tension on the proximal phalangeal splint upon the respective tightening and loosening of the strap.

12 Claims, 8 Drawing Figures

U.S. Patent
Jun. 26, 1984
4,456,002
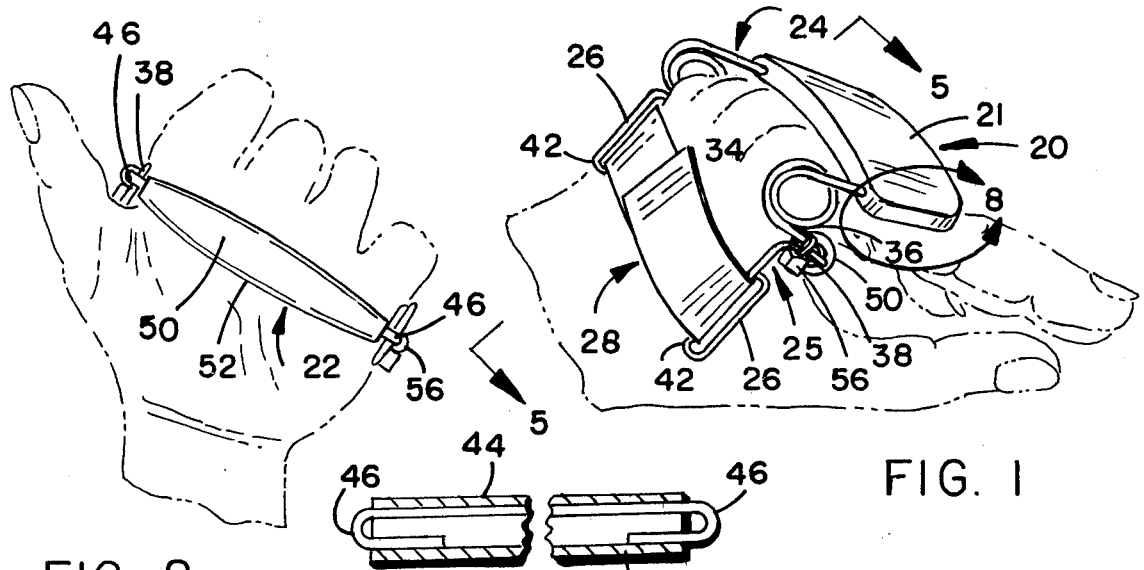
FIG. 1
FIG. 2
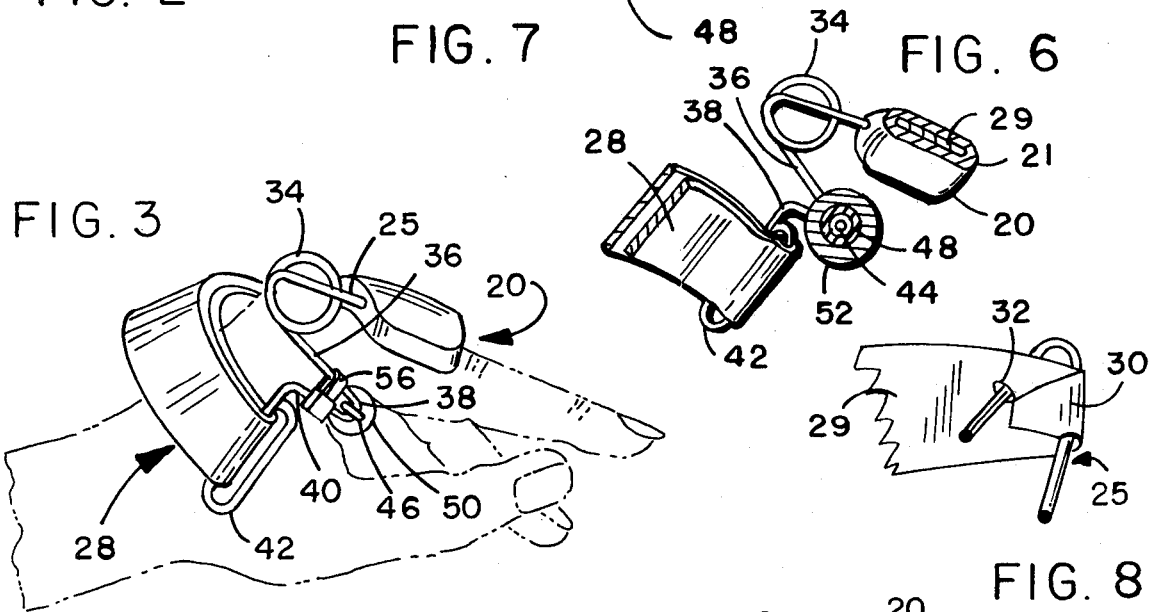
FIG. 7
FIG. 6
FIG. 3
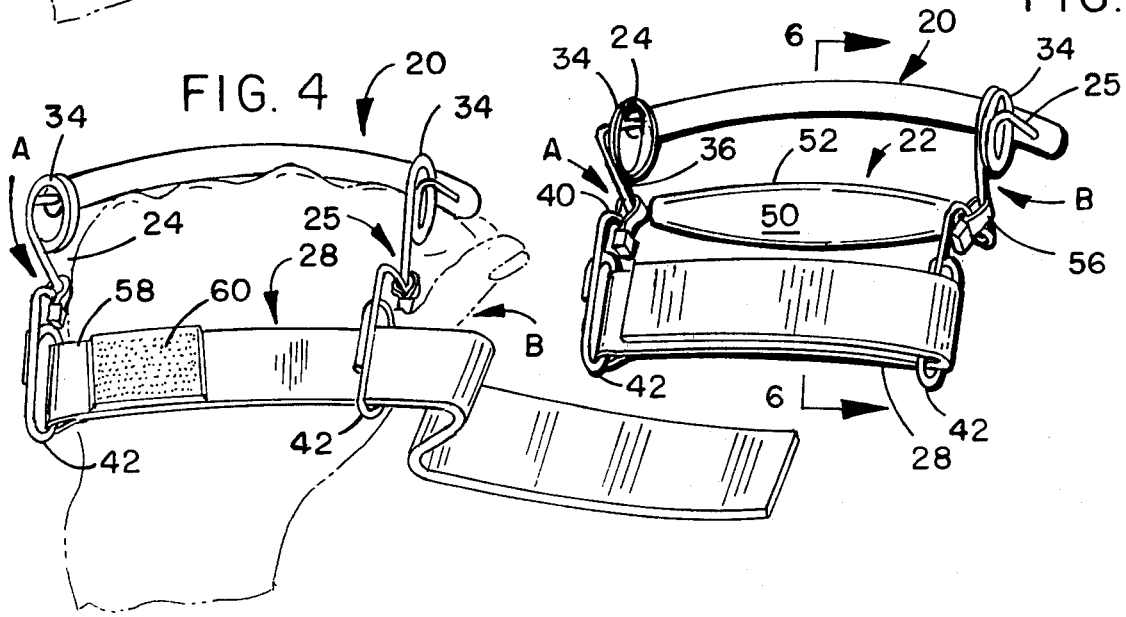
FIG. 8
FIG. 4

SPRING METACARPOPHALANGEAL FLEXION SPLINT (KNUCKLE SPLINT)

BACKGROUND OF THE INVENTION

1. Field Of The Invention

This invention relates to the field of hand splints and is particularly directed to a new spring metacarpophalangeal flexion splint as hereinafter described.

2. Description Of The Prior Art

Until the present time, metacarpophalangeal flexion splints have been comprised of cushioned steel bands or straps located on the proximal phalanges and back of the hand and which are interconnected to a palm piece. The tension on the device is provided by means of rubber bands which are connected to or looped over angled projections from the device. The implacement of the rubber bands is often difficult, especially for those with bilateral hand injuries. In addition, the protruding portions of these devices have a tendency to catch on things during the normal motion of the hand. In addition, felt is often used as a cushioning material which is not waterproof or readily cleaned, so that cleanliness is not easily maintained. Furthermore, the palm piece utilized in prior art devices consists of a flat piece of wire or steel which is lacking in comfort since it does not accommodate the normal palmar arch of the hand. Furthermore, such devices are not aligned with the distal palmar flexion crease of the hand.

SUMMARY OF THE INVENTION

The spring metacarpophalangeal flexion splint of this invention overcomes the deficiencies of the prior art devices by providing a splint which is relatively streamlined by comparison to prior art devices. In addition, the padding materials utilized are waterproof and washable. Preferably, the padding material is a heat-sealed closed cell polyethylene foam which completely encloses the support materials. The design is especially desirable since it permits the normal motion of the hand to take place. Furthermore, the splint is easily put on and taken off with a minimum of effort, is easily cleaned, and has a particular feature of being capable of adjustment of the tension of the device by the loosening or tightening of the dorsal strap.

A further advantage of the device is the fact that the proximal phalangeal piece is formed of a manually bendable material such as aluminum which can easily be adjusted to provide individual fit without requiring special tools.

As used herein, MP means metacarpophalangeal and is interchangeable therewith.

The spring MP flexion splint of the invention is comprised of a manually bendable proximal phalangeal piece which is adapted to contact, cover and follow the curve of the proximal phalanges of the fingers. Preferably, it is formed with a resilient metal, for example, aluminum, which is entirely enclosed and cushioned by a pliant cushioning material, such as polyethylene foam. The splint also includes a palm piece which is adapted to fit into the palmar arch and not interfere with the distal palmar crease of the hand. It is formed of a substantially rigid tube, which is covered with a pliant cushioning material, such as a polyethylene foam which is built up in the center thereof to accommodate the palmar arch. The rigid tube, which is preferably comprised of nylon, holds and contains a length of spring wire which has its ends bent over upon itself for a portion of its length which bent-over portions extend partially out of the ends of the nylon tube. These bent-over areas form loops which permit the palm piece to be attached to the device, as hereinafter explained.

Uniting the proximal phalangeal piece and the palm piece are a pair of spaced apart generally parallel spring wires which are generally laterally disposed with respect to the hand. The wires provide the required spring tension between the proximal phalangeal and palm pieces to force the proximal phalangeal and palm pieces together which force is resisted by the action of the hand or the stiffness of the joints. The tension is provided by means of a number of coiled loops of the spring wire which are spaced from the proximal phalangeal piece and from the palm piece. An acute bend of the spring wire provides a means for attachment of the palm piece which is held in place by means of a cable tie. The portion of the wire which extends from the palm piece is bent upon itself to form a closed loop, providing a means of attachment of a dorsal strap which is threaded through the loops and attached to itself by any conventional means, preferably a Velcro (a registered trademark) hook and brushed nylon material. It is the loosening and tightening of this strap which adjusts the tension of the device.

The splint is useful in the treatment of traumatic injuries, fractures, nerve injuries, burns and other disabilities where flexion ability of the MP joints is impaired.

BRIEF DESCRIPTION OF THE DRAWINGS

The invention will be more clearly understood by reference to the description below, taken in conjunction with the accompanying drawings wherein:

FIG. 1 shows a perspective view of the spring MP flexion splint of the invention implaced upon a hand;

FIG. 2 shows a view of the underside of the hand with the spring MP flexion splint implaced thereon;

FIG. 3 shows a side view of the spring MP flexion splint implaced on a hand;

FIG. 4 shows a rear view of the spring MP flexion splint implaced on a hand with the dorsal strap in the open position;

FIG. 5 shows a perspective view of the spring MP flexion splint of the invention as shown in the view 5—5 of FIG. 1 but removed from the hand;

FIG. 6 shows a cross section taken along the line 6—6 of FIG. 5;

FIG. 7 shows a detail of the palm piece of the invention with the padding material and a portion of the tube removed; and, FIG. 8 shows a detail of the proximal phalangeal piece of the device of FIG. 1 as viewed through enclosure 8 with the padding material removed.

DESCRIPTION OF THE PREFERRED EMBODIMENTS

Referring now to FIGS. 1 and 2, there is shown the spring MP flexion splint of the invention implaced on a hand. As shown, the splint is composed of a proximal phalangeal piece 20 and a palm piece 22 which are joined together by means of spring wires 24 and 25. Spring wires 24 and 25 include extensions 26 which are bent to form loops 42 through which is threaded dorsal strap 28.

As shown, the proximal phalangeal piece 20 is curved to follow the curve of the proximal interphalangeal joints of the hand. The proximal phalangeal piece 20 includes a manually bendable metal strip 29, seen in FIGS. 6 and 8. It is preferably formed of aluminum, which is fully enclosed in a sandwich relationship with a foamed cushioning material 21, preferably a heat sealable, closed cell polyethylene foam. The pair of spring wires 24 and 25 hold the proximal phalangeal piece 20 in place as shown in FIG. 8. Each wire is held in place by means of a crimped over area 30 and an aperture 32 through which the end of the spring wire 25 passes. If desired, the crimped over area 30 and the end of the spring wire 25 can be covered with a strip of protective tape such as duct tape, not shown. This eliminates wear points over these areas.

When implaced on the hand, the proximal phalangeal piece 20 can be manually bent to provide an individual fit to the hand to be splinted. If necessary, this bend can be changed at any future time as required, to accommodate swelling and the like.

As shown, the spring wires 24 and 25 which are preferably made of stainless steel, are disposed laterally with respect to the hand. Upon leaving the proximal phalangeal piece 20, the spring wires 24 and 25 are formed into a coil 34. The coil 34 is followed by an extension of the wires 24 and 25 which leads downwardly from the coil 34 to form one leg of a hairpin type bend 38 of which the other leg is at 40. Each wire 24 and 25 is then bent at substantially a right angle to leg 40 after which it is bent upon itself in the manner of a loop 42 which is sized to accommodate the dorsal strap 28.

As shown especially in FIGS. 2, 6 and 7 the palm piece 22 is made up of a single length of spring wire 44 which has bent over ends 46. The wire 44 is encased in a rigid tube 48, preferably of nylon. The rigid tube 48 with the exception of the bent over areas 46 of the wire 44 are covered with a resilient padding material 50 which is thicker in the central area 52 to accommodate and fill in the palmar arch of the hand.

The palmar piece 22 is attached to the spring wire 24 at the hairpin bend 38 by means of the bent over areas 46 of the wire 44. In order to prevent sliding of the bent over area 46 over the angle 38, a cable tie 56 is provided as shown in FIG. 3 which surrounds legs 36 and 40.

The dorsal strap 28 is threaded through loops 42 of the wires 24 and 25. One of the ends of the strap 28 is attached to itself by means of adhesive or stitching as at 58. The remaining end of the strap 28 is threaded through the other loop 42 which is then folded back over itself and secured to a Velcro hook strip 60 as shown in FIG. 4. Preferably, the Velcro strip is formed of a soft, cushioning type of material such as, for example, a piece of foam material having a brushed nylon covering over one side, which will attach to the velco hooks upon contact therewith.

The lateral spring wires 24 and 25 exert a force or tension which urges the palm piece and the knuckle piece together. This force is resisted by the action of the fingers and especially the proximal interphalangeal joints. This tension can be increased by the tightening of the dorsal strap; or it can be decreased by loosening of the dorsal strap.

The tightening of the dorsal strap pulls the strap loops and wires upwardly to increase tension on the device. During use, the purpose of the splint is to flex the metacarpophalangeal joints.

It is apparent that the adjustment of tension on the splint is quite a simple maneuver and does not require complicated finger dexterity in order to attach the splint. Thus, the spring MP flexion splint is easily put on and taken off, which encourages the use thereof. In addition, since the splint does not restrict normal hand movement during use, the patient is also encouraged to wear it.

A particular advantage of the spring MP flexion splint of the invention is the design of the palm piece 22. Not only is the extra padding 52 of the palm piece 22 provided to accommodate the palmar arch, but the alignment of the palm piece as shown in FIG. 2 follows the palmar crease of the hand. This provides a better fit and a better function to the spring MP flexion splint of the invention.

The placement of the palm piece in alignment with the palmar crease is accomplished by using a slightly shorter length of spring wire coupled with a slightly smaller coil on the ulnar side of the hand and a relatively longer length of spring wire and a relatively larger coil on the radial side of the splint. Not only does this effectively align the palm piece 22 with the palmar crease, but also aligns the proximal phalangeal piece 20 with the proximal interphalangeal joints of the hand which lie at a slight angle from the radial side of the hand to the ulnar side of the hand.

In the splint shown in FIGS. 4 and 5 for example, the spring wire 24 on the ulnar side of the splint indicated at A is shorter than the spring wire 25 on the radial side of the splint as indicated at B.

While the preferred cushioning material is a polyethylene foam, other types of foam can also be used such as, for example, polypropylene foam, ionomer foam, polystyrene foam, polyurethane foam, P.V.C. (polyvinylchloride) flexible foam and silicone foam. The above mentioned plastic foams are intended to be exemplary and are not intended to in any way limit the type of cushioning material which can be used in the invention. Not all of the above mentioned foams are capable of being heat sealed and might require an adhesive to improve the bonding of the foam layers together. This should in no way limit the use thereof.

The main advantages of the use of polyethylene foam include the characteristics of low water absorption, good energy absorption, water vapor barrier, compressability, smooth surface, thermal stability at temperatures up to 215 degrees F., and a high ratio of tensile and shear strength to weight compared to other resilient foams. In addition, the capability of being heat sealed also makes it additionally attractive.

Although the dorsal strap has been shown to be composed of a padded brushed nylon strap in conjunction with Velcro hooks, other types of fastening means can also be used. For example, Velcro patches can be sewn to cotton straps, or in place of the Velcro patches, there can be substituted buckles, snaps, buttons, hooks, and the like. These materials are not as preferred, since they do not provide the easy adjustment which is obtainable through the use of Velcro patches.

Similarly, while the preferred support material for the proximal phalangeal piece is aluminum because of its light weight, low cost and malleable characteristics, other types of metals can be substituted therefor. Such metals should be lightweight reinforcing metals which provide the strength and malleable characteristics of aluminum, such as, for example among others, copper, steel, brass and the like.

In place of the metal, there could also be used a molded plastic, preferably a malleable or resilient type of rubber.

The spring MP flexion splint which is illustrated in the drawing is a left hand splint. Right handed splints would be the mirror image of the left hand splint.

Various other modifications of the invention are contemplated which would be obvious to those skilled in the art and can be resorted to without departing from the spirit and scope of the invention as defined by the following claims.

We claim:

1. A spring metacarpophalangeal flexion splint comprising:
   a cushioned manually bendable proximal phalangeal piece adapted to contact, cover and follow the curve of the proximal interphalangeal joints of the hand;
   a palm piece adapted to fit into the palmar arch and palmar crease of the hand and including a substantially rigid tube covered with a pliant cushioning material;
   a pair of spaced spring wires, connecting said proximal phalangeal piece and said palm piece and which are disposed generally laterally with respect to the hand and providing spring tension between said proximal phalangeal and palm pieces to force said proximal phalangeal and palm pieces together, each of said spring wires having a projection extending from said palm piece;
   strap attachment means on the ends of said projections; and,
   an adjustable dorsal strap between said strap attachment means to permit increase and decrease of tension of the spring metacarpophalangeal flexion splint upon the respective tightening and loosening of said strap.

2. A spring metacarpophalangeal flexion splint as claimed in claim 1 wherein each of said spring wires connecting said proximal phalangeal piece and said palm piece comprises:
   a length of spring wire attached at one end to said proximal phalangeal piece and at the opposite end to said dorsal strap, the intermediate length of wire being bent upon itself to form a coil spring spaced from said proximal phalangeal piece and from said palm piece;
   said wire extending from said coil being crimped to form an acute angle spaced from said coil, said acute angle being formed of a downward leg from said coil and an upward leg which is further bent approximately normal to said upward leg to form a loop, said coil angles and loop lying substantially in the same plane; and,
   said acute angle forming a means for attachment of said palm piece and said loop forming a means for attachment of said dorsal strap.

3. A spring metacarpophalangeal flexion splint as claimed in claim 2 wherein:
   said proximal phalangeal piece is formed of a resilient metal strip substantially covered with a pliant cushioning material.

4. A spring metacarpophalangeal flexion splint as claimed in claim 3 wherein:
   the spring wire disposed on the splint which is worn on the ulnar side of the hand is sized slightly shorter and has a slightly smaller coil such that the palm piece is aligned with the palmar crease of the hand and the proximal phalangeal piece is aligned with the proximal interphalangeal joints of the hand.

5. A spring metacarpophalangeal flexion splint as claimed in claim 4 wherein said palm piece further comprises:
   a length of wire having a bent-over hair pin angle at each end which is disposed within a rigid tube and slightly extending therefrom, said angles being looped around said spring wire at its acute angle for attachment thereto; and,
   a cable tie snugly fitted around said acute angle loop to maintain said palm piece wire extension at the base of said tension wire acute angle.

6. A spring metacarpophalangeal flexion splint as claimed in claim 1 wherein:
   said pliant cushioning material surrounding said rigid tube is thicker in the central area of its length to fill in the natural palmar arch of a hand.

7. A spring metacarpophalangeal flexion splint as claimed in claim 5 wherein:
   said proximal phalangeal piece is crimped over at its ends and includes a small aperture; and,
   the ends of said spring wire are bent into an acute angle, one leg of which is held by said crimped over areas of said metal strip and the remaining leg of said angle passes through and is held in place by said aperture.

8. A spring metacarpophalangeal flexion splint as claimed in claim 8 further comprising:
   a strip of protective tape overlying said aperture and crimped over areas of said proximal phalangeal piece.

9. A spring metacarpophalangeal flexion splint as claimed in claim 8 wherein:
   said metal strip is of aluminum;
   said resilient material is a heat sealable closed cell polyethylene foam;
   said rigid tube is nylon; and,
   said spring wire is of stainless steel.

10. A spring metacarpophalangeal flexion splint as claimed in claim 1 wherein:
    said dorsal strap is formed of a lightly padded brushed nylon which adjustably attaches to a Velcro hook area on said strap.

11. A spring metacarpophalangeal flexion splint comprising:
    a manually bendable proximal phalangeal piece adapted to contact, cover, and follow the curve of the proximal interphalangeal joints of the hand, said proximal phalangeal piece comprising a resilient metal strip which is substantially enclosed with a pliant cushioning material;
    a palm piece adapted to fit into the palmar arch and crease of the hand, said palm piece comprising a substantially rigid tube covered with a pliant cushioning material and a length of spring wire having a bent-over hairpin angle at each end which wire is disposed within said tube with said angles protruding therefrom to act as an attachment means;
    a pair of spaced spring wires connecting said proximal phalangeal piece and said palm piece and which are disposed generally laterally with respect to the hand, each of said spring wires comprising a length of spring wire attached at one end to said proximal phalangeal piece, the length of wire extending from said proximal phalangeal piece being bent upon itself to form a coil spring spaced from said proximal phalangeal piece and from said palm piece, said wire extending from said coil spring being crimped to form an acute angle spaced from said coil, said acute angle being formed of a downward leg from said coil and an upward leg which is further bent approximately normal to said upward leg to form a loop, said coil angles and loop lying substantially in the same plane, said acute angle being threaded through said bent-over areas of said palm piece wire;

the spring wire disposed on the splint which is worn on the ulnar side of the hand being sized slightly shorter and having a slightly smaller coil such that the palm piece is aligned with the palmer crease of the hand and the proximal phalangeal piece is aligned with the proximal interphalangeal joints of the hand; and, a dorsal strap threaded through said wire loops for increase and decrease of tension of the spring metacarpophalangeal flexion splint upon the respective tightening and loosening of said strap.

12. A spring metacarpophalangeal flexion splint as claimed in claim 11 wherein:

said metal strap is aluminum;

said spring wire is stainless steel; and, said cushioning material is a heat sealable polyethylene foam.

* * * * *